United States Patent
Barton et al.

(10) Patent No.: US 12,239,287 B2
(45) Date of Patent: Mar. 4, 2025

(54) CELL-COLLECTING FALLOPOSCOPE AND METHOD FOR OVARIAN CANCER DETECTION

(71) Applicant: Arizona Board of Regents on Behalf of the University of Arizona, Tuscon, AZ (US)

(72) Inventors: Jennifer Barton, Tucson, AZ (US); Kelli Kiekens, Tucson, AZ (US); Gabriella Romano, Tempe, AZ (US); Swati Chandra, Tucson, AZ (US); Steven Santaniello, Tucson, AZ (US); Richard Cordova, Tucson, AZ (US); David Vega, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 360 days.

(21) Appl. No.: 17/753,578

(22) PCT Filed: Sep. 9, 2020

(86) PCT No.: PCT/US2020/049927
§ 371 (c)(1),
(2) Date: Mar. 8, 2022

(87) PCT Pub. No.: WO2021/050537
PCT Pub. Date: Mar. 18, 2021

(65) Prior Publication Data
US 2022/0330792 A1   Oct. 20, 2022

Related U.S. Application Data
(60) Provisional application No. 62/897,744, filed on Sep. 9, 2019.

(51) Int. Cl.
*A61B 1/00* (2006.01)
*A61B 1/005* (2006.01)
(Continued)

(52) U.S. Cl.
CPC ........ *A61B 1/00096* (2013.01); *A61B 1/0057* (2013.01); *A61B 1/05* (2013.01);
(Continued)

(58) Field of Classification Search
CPC ..... A61B 1/00096; A61B 1/0057; A61B 1/05; A61B 1/0638; A61B 1/07; A61B 10/0291;
(Continued)

(56) References Cited

U.S. PATENT DOCUMENTS 5,364,345 A    11/1994  Lowery et al.
5,368,598 A *  11/1994  Hasson ............ A61B 17/4241
                                              606/119

(Continued)

FOREIGN PATENT DOCUMENTS

WO    1992015238 A1    9/1992
WO    2013029047 A1    2/2013

OTHER PUBLICATIONS

PCT Application No. PCT/US20/49927, International Search Report and Written Opinion dated Feb. 8, 2021, 7 pages.
(Continued)

*Primary Examiner* — Bo Joseph Peng
(74) *Attorney, Agent, or Firm* — Cozen O'Connor

(57) ABSTRACT

A falloposcope is described, and a method of screening a patient for fallopian tube and/or ovarian cancer with the falloposcope. The falloposcope can perform optical imaging, including fluorescence imaging and/or optical coherence tomography (OCT), and optionally include a channel for a sampling wire, within a diameter of about 0.7 milli-
(Continued)

meter. The method includes inserting the falloposcope through a lumen of vagina, cervix, uterus, and fallopian tube so a tip of the falloposcope is in proximity to a first fallopian tube or ovary of the patient; providing fluorescence stimulus wavelength through an illumination fiber of the falloposcope while imaging light at fluorescence emission wavelength through a coherent fiber bundle to form fluorescence emissions images; and determining suspect tissue. Then the sampling wire is used to collect cells from the suspect tissue for karyotype and other analysis.

13 Claims, 12 Drawing Sheets

(51) Int. Cl.
    *A61B 1/05*          (2006.01)
    *A61B 1/06*          (2006.01)
    *A61B 1/07*          (2006.01)
    *A61B 10/02*        (2006.01)
    *A61B 10/04*        (2006.01)

(52) U.S. Cl.
    CPC .............. *A61B 1/0638* (2013.01); *A61B 1/07* (2013.01); *A61B 10/0291* (2013.01); *A61B 10/04* (2013.01); *A61B 1/00082* (2013.01)

(58) Field of Classification Search
    CPC ................ A61B 10/04; A61B 1/00082; A61B 2010/0216
    See application file for complete search history.

(56) References Cited

U.S. PATENT DOCUMENTS

| | | | |
|---|---|---|---|
| 5,413,108 A | 5/1995 | Alfano | |
| 5,716,321 A | 2/1998 | Kerin | |
| 5,807,239 A | 9/1998 | DiBernardo | |
| 6,456,769 B1 | 9/2002 | Furusawa | |
| 8,025,656 B2 * | 9/2011 | Gruber | A61B 17/12131 |
| | | | 604/27 |
| 8,235,048 B2 * | 8/2012 | McGuckin, Jr. | A61F 6/225 |
| | | | 606/135 |
| 2002/0193672 A1 | 12/2002 | Walsh | |
| 2003/0051735 A1 * | 3/2003 | Pavcnik | A61B 17/0057 |
| | | | 128/831 |
| 2003/0120176 A1 | 6/2003 | Reeves et al. | |
| 2004/0122286 A1 | 6/2004 | Kamrava | |
| 2004/0245350 A1 | 12/2004 | Zeng | |
| 2004/0249243 A1 | 12/2004 | Kleiner | |
| 2005/0215911 A1 | 9/2005 | Alfano | |
| 2006/0066865 A1 | 3/2006 | Tsujita | |
| 2008/0135053 A1 * | 6/2008 | Gruber | A61F 6/208 |
| | | | 606/119 |
| 2010/0002560 A1 * | 1/2010 | Yamasaki | G11B 7/1378 |
| 2012/0059220 A1 | 5/2012 | Holsing et al. | |
| 2012/0140301 A1 | 6/2012 | Xu | |
| 2012/0143029 A1 * | 6/2012 | Silverstein | A61B 8/0891 |
| | | | 600/374 |
| 2012/0277528 A1 | 11/2012 | Qiao | |
| 2013/0226131 A1 | 8/2013 | Bacino et al. | |
| 2013/0324858 A1 | 12/2013 | Xu | |
| 2014/0088459 A1 | 3/2014 | Roush et al. | |
| 2014/0180004 A1 | 6/2014 | Yamashita | |
| 2014/0378843 A1 | 12/2014 | Valdes | |
| 2015/0119708 A1 | 4/2015 | Sachse | |
| 2015/0253240 A1 | 9/2015 | Rowe | |
| 2015/0351729 A1 | 12/2015 | Chin et al. | |
| 2018/0014773 A1 * | 1/2018 | Barton | A61B 5/0066 |

OTHER PUBLICATIONS

PCT Application No. PCT/US2016/016456, International Search Report, dated May 24, 2016, 3 pages.
J.F. Kerin, Chapter 10, Falloposcopy, Royal College of Obstetricians and Gynaecologist 1992, pp. 169-184.

\* cited by examiner

```
┌─────────────────────────────────────────────┐
│ Insert Hysteroscope through Vagina Into     │
│ Uterus and Visualize Fallopian Tube         │
│ Openings. 702                               │
└─────────────────────────────────────────────┘
                      │
┌─────────────────────────────────────────────┐
│ Apply visible light through illumination    │
│ fiber. Use images taken through the fiber-  │
│ optic bundle of the falloposcope, and the   │
│ hysteroscope, and manipulation of steering  │
│ wires of the falloposcope, to thread the    │
│ falloposcope through through the fallopian  │
│ tube to position the tip of the falloposcope│
│ at a viewing position adjacent an ovary or  │
│ lesion in the fallopian tube 704            │
└─────────────────────────────────────────────┘
                      │
┌─────────────────────────────────────────────┐
│ Visual inspection of fallopian tube interior│
│ during insertion of falloposcope through    │
│ fallopian tube, to detect suspect tissue in │
│ fallopian tube; inspect tissue and obtain   │
│ cell sample if found. 706                   │
└─────────────────────────────────────────────┘
                      │
┌─────────────────────────────────────────────┐
│ At each viewing position, Illuminate with   │
│ multiple wavelengths of fluorescent         │
│ stimulus light, and image at fluorescent    │
│ emissions wavelengths, to determine         │
│ presence of suspect tissue. 708             │
└─────────────────────────────────────────────┘
                      │
┌─────────────────────────────────────────────┐
│ Perform optical coherence tomography or cell│
│ sampling to confirm or deny cancerous       │
│ nature of the suspect tissue. 710           │
└─────────────────────────────────────────────┘
                      │
┌─────────────────────────────────────────────┐
│ Repeat for second fallopian tube or ovary,  │
│ if present 712                              │
└─────────────────────────────────────────────┘
```

Fig. 7

Wire Shape Comparison Diagram

CELL-COLLECTING FALLOPOSCOPE AND METHOD FOR OVARIAN CANCER DETECTION

PRIORITY CLAIM

The present application claims priority to U.S. Provisional Patent Application No. 62/897,744 filed 9 Sep. 2019. The entire contents of the aforementioned provisional application are incorporated herein by reference.

GOVERNMENT INTEREST

This invention was made with government support under Grant Nos. P30 CA023074, R21 CA229707, and U54 EB015403, awarded by the National Institutes of Health and Grant Nos. W81XWH-13-1-0131 and W81XWH-18-1-0371 awarded by ARMY/MRMC. The government has certain rights in the invention.

BACKGROUND

Ovarian cancer is often detected at an advanced stage in part because symptoms are mild at early stages, and because there has been no readily available, low-cost, screening test. The risk of contracting ovarian cancer over a lifetime is about one in seventy, but is many times higher in high risk women such as those afflicted with the BRCA-1 or BRCA-2 genes. Seventy percent of women who develop this cancer die from it. Five-year survival for ovarian cancer following diagnosis at advanced stages could be increased from the current 50% to greater than 90% if the disease can be detected when still confined to the ovary.

Visual inspection of the ovaries in high risk women is possible with laparoscopy, but laparoscopy typically requires at least one incision through the abdominal wall with attendant pain, healing time, risk of infection, and anesthesia requirements; laparoscopic inspection of the ovaries is therefore uncommon. Further, some high-grade serous ovarian carcinomas have their origins in the fallopian tubular or endometrial epithelium, and may be missed by laparoscopic inspection.

The typical human female reproductive system 100 is illustrated in FIG. 1. A vagina 102 is a tubular structure that has an opening 104 outside the body and extends to the cervix 106 at the mouth of uterus 108. The uterus has a central passage or lumen 110 that communicates through the cervix 106 to a lumen of the vagina 102 and extends to and forks into a pair of fallopian tube mouths 112. The first 114 and second 116 fallopian tubes, each having a lumen 118, extend laterally from the uterus and terminate in ciliated fimbriae 120. The ciliated fimbriae are in close proximity to and partially surround a first 122 and second 124 ovary and serve to collect ova released by the ovary and direct them into the lumen on the associated fallopian tube. Depending on age and reproductive state of the patient, there may be one or more benign cysts or developing ova (not shown) on or near the ovarian surface. In some patients, there may be suspect tissue 126 requiring evaluation on or near the ovarian surface or in the lumen of the fallopian tubes 118. While lumens of many portions of the reproductive system are considerably larger, the lumens 118 of fallopian tubes 114, 116 may only be a millimeter in diameter at their narrowest point. Typical endoscopes, as used for colonoscopy and upper gastrointestinal tract investigations, are approximately a centimeter in diameter, far too large to pass comfortably through a normal fallopian tube. While bronchoscopes are typically smaller in diameter than colonoscopes, they are typically too large to comfortably pass through fallopian tubes.

SUMMARY

A falloposcope is described, as is a method of using the falloposcope to screen a patient for fallopian tube and/or ovarian cancer. The falloposcope has an optical imaging subsystem capable of performing optical and fluorescence imaging, and an optical coherence tomography (OCT) channel, all in a diameter less than 1 millimeter (mm) and in a particular embodiment between 0.7 and 0.8 mm. The method includes inserting the falloposcope through a lumen of vagina, cervix, uterus, and fallopian tube such that a tip of the falloposcope is in proximity to a first fallopian tube or ovary of the patient; providing fluorescence stimulus wavelength through one or more illumination fibers of the falloposcope, while imaging light at fluorescence emission wavelengths through a coherent fiber bundle to form fluorescence emissions images; and determining suspect tissue from the fluorescence emission images. The OCT channel is also used to examine tissue, both to determine suspect tissue and analyze suspect tissue from fluorescence observations.

In embodiments, the falloposcope has a lumen through which a cell sampling wire passes, the cell sampling wire collects cells from an ovary or fallopian tube for culture, karyotype analysis, and other studies that may be of use in diagnosis and treatment of abnormalities including cancers. In some embodiments, this lumen is in addition to the OCT and fluorescence imaging channels, and in some embodiments this lumen may replace the OCT channel or fluorescence imaging channel.

In embodiments, the falloposcope has a mode scrambler in an illumination or efferent fiber.

In embodiments, the falloposcope uses a 3-D printed lens with a skirt that positions the lens at a fixed-focus position above the coherent fiber bundle through which images are obtained.

In an embodiment, a falloposcope has an elongated body with circumferential diameter less than one millimeter, the elongated body comprising a polymer extrusion; an efferent optical fiber extending through the elongated body from a proximal end of the elongate body to a distal end of the elongate body, the efferent optical fiber having a distal end at the distal end of the elongate body; and an illuminator coupled to the efferent fiber near the proximal end of the elongate body. The falloposcope also has at least one maneuvering wire extending through the elongate body and configured to, when pulled, bend a portion of the elongate body near the distal end of the elongate body; a lens assembly located at the distal end of the elongate body configured to focus images on a coherent fiber bundle running through the elongate body; and an electronic camera coupled to receive images from the coherent fiber bundle. The elongate body of the falloposcope has a lumen containing a cell sampling device, the cell sampling device comprising a wire, the cell sampling device extending from a sampling device handle through the elongate body from the proximal end of the elongate body to the distal end of the elongate body.

In an embodiment, a method of obtaining cells from a subject for examination includes inserting a falloposcope through a hysteroscope into a fallopian tube of a subject; extending the falloposcope through the fallopian tube to an ovary of the subject; extending a cell collecting device through a lumen of the falloposcope to collect the cells from the subject; withdrawing the cell collecting device into the falloposcope; and removing the cells from the falloposcope. The falloposcope includes an elongated body having circumferential diameter less than one millimeter, the elongated body having a core formed of a polymer extrusion; an efferent optical fiber extending through the elongated body from a proximal end of the elongate body to a distal end of the elongate body, the efferent optical fiber having a distal end at the distal end of the elongate body; an illuminator coupled to the efferent fiber near the proximal end of the elongate body; a lens assembly located at the distal end of the elongate body and configured to focus images on an image sensor selected from the group consisting of a camera with a coherent fiber bundle running through the elongate body, and an electronic image sensor; and the elongate body has a lumen containing the cell sampling device, the cell sampling device comprising a wire, the cell sampling device extending from a sampling device handle through the elongate body from the proximal end of the elongate body to the distal end of the elongate body.

In another embodiment, a falloposcope includes an elongated body having circumferential diameter less than one millimeter, the elongated body comprising a polymer extrusion; a light emission port at a distal end of the elongate body, the elongate body also having a proximal end, at least one maneuvering wire extending through the elongate body and configured to, when pulled, bend a portion of the elongate body near the distal end of the elongate body; an electronic camera located at the distal end of the elongate body; wherein the elongate body has a lumen containing a cell sampling device, the cell sampling device comprising a wire, the cell sampling device extending from a sampling device handle through the elongate body from the proximal end of the elongate body to a lateral sampling device port near the distal end of the elongate body.

BRIEF DESCRIPTION OF THE FIGURES

FIG. 7 is a flowchart of use of the falloposcope to screen a patient.

DETAILED DESCRIPTION OF THE EMBODIMENTS

A small diameter steerable endoscope, known herein as a falloposcope, has diameter of less than two millimeters and preferably less than one millimeter, and in a particular embodiment of seven- to eight-tenths of a millimeter, is capable of being inserted through narrow openings and performing visual inspection of objects to detect abnormalities. In particular, the falloposcope is adapted to be inserted through the natural orifice of the lumens of vagina, uterus, and fallopian tubes to observe objects such as the ovaries and portions of the fallopian tubes, and detect abnormalities such as early stage ovarian cancer. The falloposcope is equipped with multispectral fluorescence imaging (MFI) and optical coherence tomography (OCT).

MFI utilizes endogenous fluorophores (such NADH and tryptophan-rich proteins such as collagen) for contrast. MFI requires a fluorescence stimulus-wavelength light source, together with multiband, wavelength-selective, visual observation apparatus for viewing a targeted ovary at multiple emissions wavelengths. With the use of ultraviolet stimulus wavelengths, between 240 and 400 nanometers (nm), or visible wavelengths between 400-550 nm in MFI, it is possible to detect fluorescence due to proteins. Using ratios of the autofluorescence produced at each pixel at each of several stimulus wavelengths and at more than one, discrete emissions wavelength, and using other image processing techniques, combined false-color images having significantly enhanced contrast of lesions are generated. The combined false-color images are presented to the surgeon to permit location of suspected tissue abnormalities for which further investigation by single-point OCT is performed. In some instances where sufficient abnormalities of tissue are seen under MFI, further investigation by laparoscopic biopsy or other techniques may be advised.

OCT uses near-infrared light to build up cross sectional images up to about 2 millimeters (mm) deep in tissue with about 3-20 micron (µm) resolution. It is anticipated that OCT will be performed at planned viewing locations, as well as locations where the surgeon sees suspect tissues in the combined MFI images, and where the surgeon sees suspect tissues in optical images.

The falloposcope is also capable of obtaining optical images when visible light illumination is provided, such that the surgeon may use such optical images to guide insertion and manipulation of the falloposcope to position the falloposcope head at particular observation points. In addition to performing MFI and OCT at preplanned observation points, suspect tissues seen in optical images obtained while positioning the falloposcope head may also be inspected with MFI and/or OCT modes as deemed necessary by the surgeon.

Experiments have shown that MFI and OCT observations can distinguish between normal and cancerous tissue in ex vivo human ovarian and fallopian tube surgical samples.

System Characteristics

Figure 1:
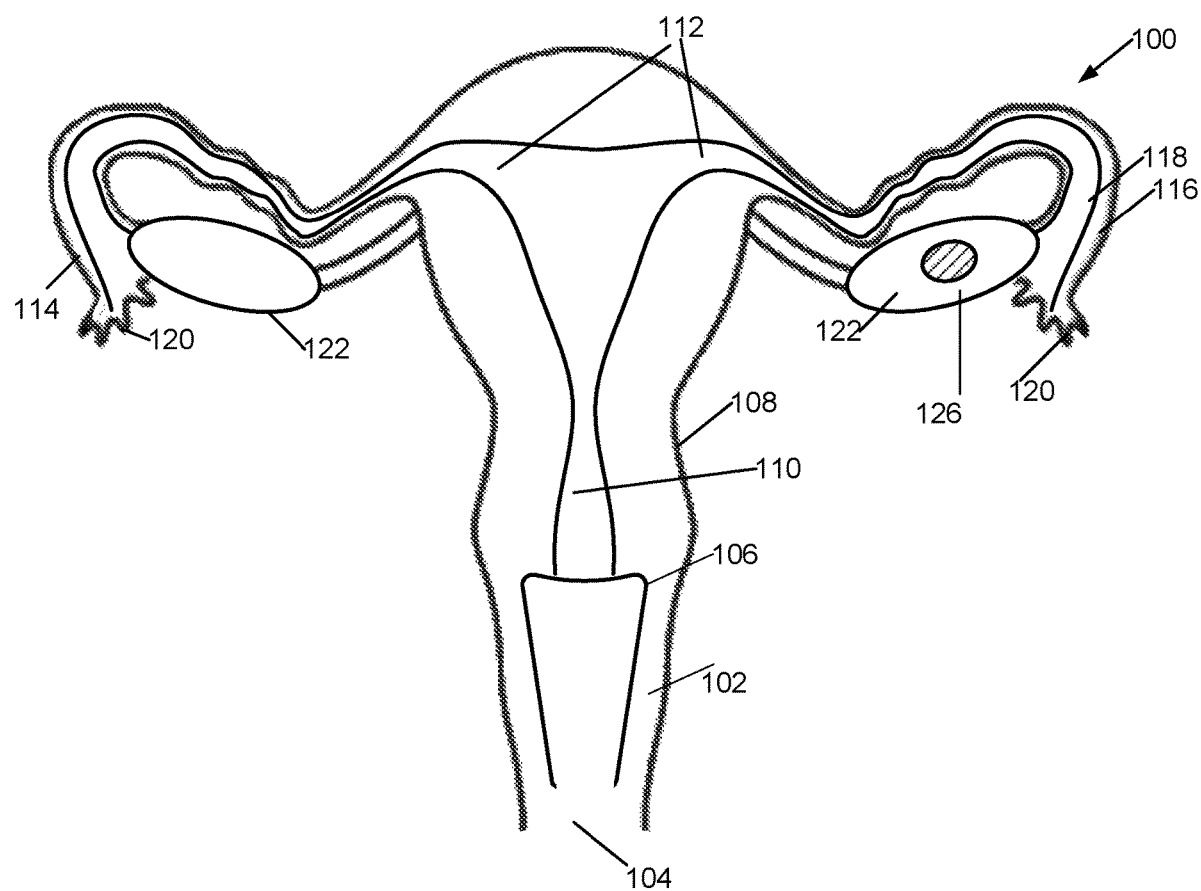
FIG. 1 is a sketch of the female reproductive system, showing lumens of the vagina, uterus, fallopian tube, and illustrating the ovaries.
Figure 2:
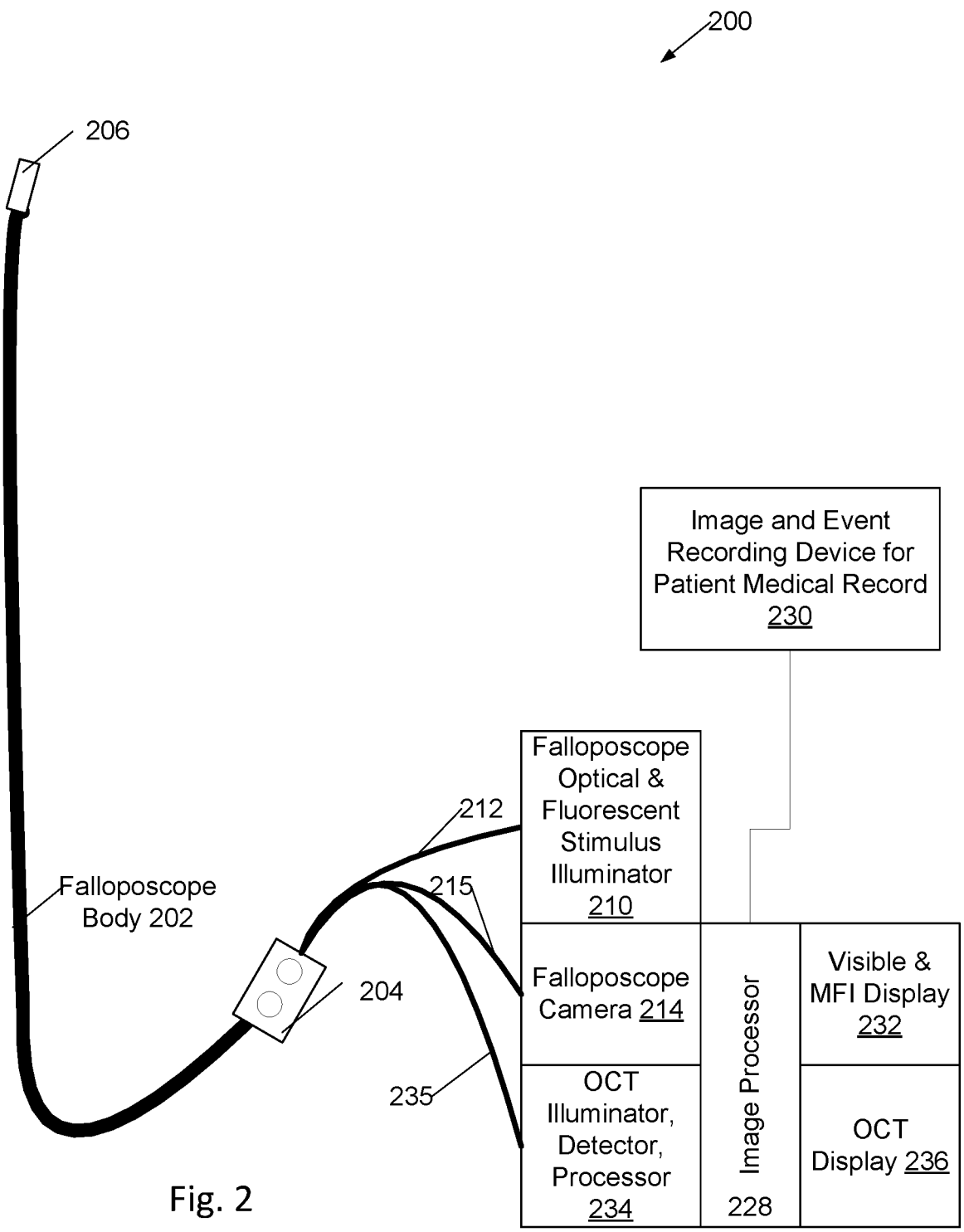
FIG. 2 is a schematic diagram of one falloposcope, in an embodiment.

The falloposcope system 200 is illustrated in FIG. 2. A falloposcope body 202 extends from a proximal end steering handle 204 to a distal-end falloposcope head or tip 206; body 202, as detailed in FIG. 3A, has one or more steering wires 352 slideably disposed in steering wire tubes 354 but fixed to the tip as pull wires (detailed as 310 in FIG. 3), at least one MFI illumination fiber 212, an MFI coherent imaging fiber bundle 215, and optionally an OCT stimulus and sensing fiber 235 in slots of a core wrapped in a moisture-resistant biocompatible sheath; the body may also have a lumen through which a cell sampling device may operate. In an alternative embodiment the sheath is formed of a shrink-wrap tubing, or may include at least one layer 362 of braided polymer fiber over a PTFE lining 364, the polymer fiber selected from a biocompatible fiber such as Pebax, Nylon, FEP, PTFE composites, and polyimide (PI). In alternative embodiments, a MFI illumination fiber bundle is provided instead of single MFI illumination fiber 212. In a particular embodiment the MFI imaging coherent fiber bundle includes 3000 fibers. In alternative embodiments, the MFI illumination fiber may be replaced with multiple fibers or a fiber bundle.

An optional connector (not shown) may be located between steering handle 204 and illuminator 210, camera 214, and OCT illuminator-detector 234 for convenience of setup and operation. This connector would divide stimulus fiber 212, coherent fiber bundle 215, and OCT fiber 235 into two portions mating at the connector.

Figure 4:
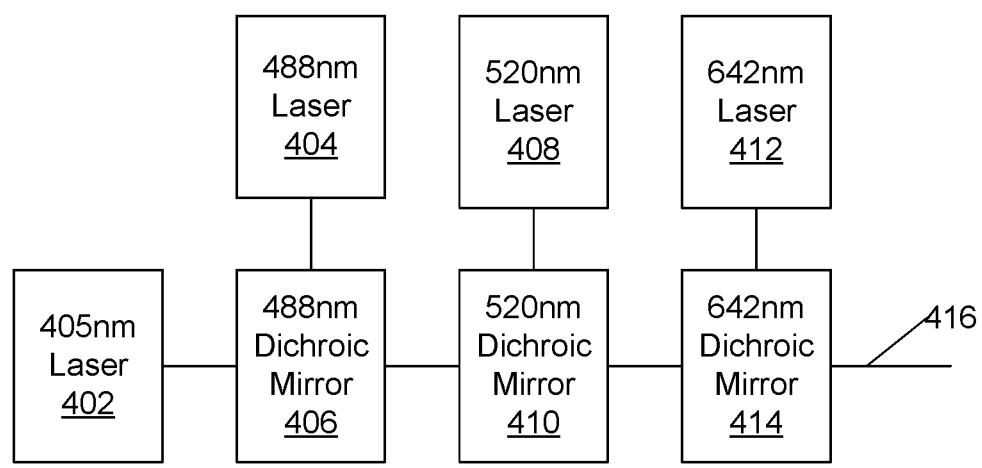
FIG. 4 is a schematic diagram of an illuminator for multispectral fluorescence imaging (MFI), the illuminator also capable of providing pseudowhite light for imaging.

The MFI illumination fiber 212 couples at its proximal end to a laser-based illumination device such as that illustrated in FIG. 4. The laser-based illumination device has illuminator 210 (FIG. 2) with separate laser sources for each fluorescence imaging wavelength, and an actual stimulus wavelength in use at a given instant of time is determined by an active laser. In illuminator 210, for example, light (FIG. 4) from a 405 nm laser is brought to a first combiner 406 having a dichroic mirror reflective to 488 nm light, the first combiner 406 combines any light from the 405 laser with light from a 488 nm laser. Light from the first combiner 406 passes to a second combiner 410 with a second dichroic mirror reflective to 520 nm light where the light from the first combiner is combined with light from a 520 nm laser. Light from second combiner 410 passes to a third combiner 414 with a dichroic mirror reflective to 642 nm light, the third combiner combines the light from the second combiner with light from a 642 nm laser 412. In an alternative embodiment, combiners 406, 410, 414 are replaced with a fiber-based wavelength-division optical multiplexor system. Light 416 from the third combiner 416 is coupled to the MFI illumination fiber 808 and used to illuminate the field of view of the falloposcope. In other embodiments additional lasers and combiners may be incorporated into the MFI illuminator, or other wavelength lasers may be substituted for the lasers specified in this paragraph. One laser at a time of the illuminator may be operated for fluorescent imaging, or multiple lasers of the illuminator may be operated to provide pseudowhite illumination for color imaging during navigation of the falloposcope through the fallopian tube to the ovary and during cell sampling.

The falloposcope 200 also has an image processor 228 coupled to receive images from the hysteroscope camera 224; this processor can provide raw and enhanced images, including enhanced images generated from ratios of reflected light and fluorescence emissions light images and from multiple stimulus wavelengths, on display 232.

The multispectral fluorescence imaging (MFI) portion of the falloposcope uses specific fluorescence excitation (or stimulus) wavelengths as generated by lasers of illuminator 210 (FIG. 2) to illuminate tissue of the patient. Light received from the tissue by lens 308 into coherent fiber bundle 215 is imaged through a filter-changer and electronic camera in falloposcope camera 214.

Each stimulus wavelength is paired with one or more emission band wavelengths; each paired emission band wavelength includes wavelengths longer than the associated stimulus wavelength and excludes the stimulus wavelength itself. For each emission wavelength band, an emissions filter in the filter changer (not shown) of the falloposcope camera 214 is provided having a passband coinciding with the emissions band, the emissions filter having a stop-band or notch that excludes light at the associated stimulus wavelength. Fluorescence emissions images are acquired by activating a laser of illuminator 210 to provide stimulus wavelength light, while imaging through the paired emissions filter.

Falloposcope camera 214 also is adapted to acquire reflected light images by activating a laser of illuminator 210 to provide light, while imaging through a neutral-density filter or a clear or empty filter. The fluorescence data provides molecular concentration information about the tissue and the reflected light data provides absorption information about the tissue.

Images captured with the falloposcope camera 214 are provided to a digital image processor 228. Using data processing techniques—including for example Mahalanobis distance, Linear Discriminant Analysis, Quadratic Discriminant analysis and Logistic Regression—tissue disease state can be discriminated with high accuracy. The image processor uses the captured image data create false color images and present these false color images to the surgeon on display 232 with enhanced visual contrast between tissue states.

In a particular embodiment, excitation or fluorescence stimulus wavelengths used for fluorescence imaging used in the analysis are 255, 280, 320, 340, 370, 400, 440, 480, and 550 nm, each ±5 nm. In a particular embodiment, the system records MFI fluorescence emissions images in emission bands of 345-410, 375-410, 410-500, 500-600, and 600-655 mu. In other embodiments it is anticipated that between 4 and 6 stimulus wavelengths are provided each of which lies in the range from 220 to 600 nm.

In experimentation, ex vivo ovarian tissue was imaged using the fluorescence excitation and emission combinations in Table 1 below. Additionally, the tissue was imaged with reflected light at 370, 400, 415, 440, 480 and 555 nm. Quadratic discriminant analysis on subsets of the 12 fluorescence images and 6 reflected light images produced 56 subsets of the image type measurements with perfect discrimination of tissue as normal, cancerous and benign conditions on 47 ovarian tissue samples. Further analysis produced an additional 1256 subsets that only failed to classify the state of one of the 47 tissue samples.

During experimentation with MLR and QDA models, image-types with excitation or emission wavelengths at or around the hemoglobin absorption peaks and troughs generally showed good tissue-type discrimination. Image-types R400 and R415, both sampling the blue side of the blood absorption peak, were included in over 92% of good QDA subsets. The illumination wavelengths of 440 and 480 nm were found in both the fluorescence and reflectance MLR models as the best predictors of tissue pathology. The process of determining variables for MLR models eliminated image-types with high covariance and thus redundant information. Since 440 nm is near the deoxyhemoglobin absorption peak while 480 nm is in a trough, the image-types acquired with these illumination wavelengths may present the strongest and weakest effects of blood absorption respectively in these samples.

Of the fluorescence image-types, F480 (fluorescent emissions at 520-655 nm when stimulated at 480 nm) was determined a strong discriminator by MLR and most frequently occurred in good QDA subsets. Unlike the other wavelengths with strong discrimination between pathology, the excitation and emission band of F480 are expected to have relatively low influence from blood absorption. The fluorescence from F480 has been shown to be higher for normal than cancer tissue in previous fiber probe studies, due to the primary excited fluorophores of FAD and collagen.

TABLE 1

MFI excitation-emission wavelength pairs

| Excitation | Emission |
|---|---|
| 280 nm | 345 nm-410 nm |
| 320 nm | 375 nm-410 nm |
| 320 nm | 410 nm-500 nm |
| 340 nm | 375 nm-410 nm |
| 340 nm | 410 nm-500 nm |
| 370 nm | 410 nm-500 nm |
| 400 nm | 600 nm-655 nm |
| 440 nm | 500 nm-600 nm |
| 440 nm | 600 nm-655 nm |
| 480 nm | 520 nm-600 nm |
| 480 nm | 600 nm-655 nm |
| 550 nm | 600 nm-655 nm |

In a particular embodiment, stimulus illuminator 210 provides a first wavelength, while camera 214 captures a first emissions wavelength image, and continues providing the first wavelength while camera 214 captures a first reflected light image. Then, stimulus illuminator 210 provides a second wavelength, while camera 214 captures a second emissions wavelength image, and continues providing the second wavelength while camera 214 captures a second reflected light. The stimulus and emissions wavelength pairs are selected from those in Table 1. The image processor 228 then uses all 4 of these images to determine suspect abnormal tissue. In alternative embodiments, additional images are captured using one or more additional stimulus wavelength/emissions wavelength pairs from Table 1, and in a particular embodiment all 12 stimulus wavelength/emissions wavelength pairs of table 1 are used.

Proximal Optics

The proximal optics of the falloposcope system includes an OCT illuminator detector and processor 234 (FIG. 2) for OCT illumination and detection; and apparatus the illuminator 210 and camera 214 for MFI illumination and detection. The OCT illuminator, detector, and processor 234 is a spectral domain system with a center wavelength of 890 nm and bandwidth of 150 nm; this OCT illuminator, detector, and processor 234 includes a source (FIG. 2) of coherent light operating at the center wavelength, this source is coupled through a fiber 235 to the OCT port 506 (FIG. 5) and thence to tissue. OCT illuminator detector and processor 234 also includes an interferometer that receives light both from the source and through fiber 235 and the OCT port from tissue, OCT results are displayed on OCT display 236.

In an embodiment, the MFI operates multiple stimulus or excitation wavelengths provided by illuminator 210 (FIG. 4) to selectively generate one of four wavelengths (405, 488, 520, and 642 nanometers) from four lasers into a 100 μm core fiber 215 that brings the light to the tip 206 of the falloposcope. Fluorescence emissions from 375 nm-650 nm and reflected light collected by the fiber bundle 215 in the distal falloposcope tip 206 are brought through a receive filter-changer (not shown) in falloposcope camera 214, see description of falloposcope camera 214 above. By selecting excitation wavelength and using appropriate emission filters, the falloposcope is tuned to particular chromophores and fluorophores of interest, some of which are associated with abnormal tissues.

Distal Optics and Mechanics

Figure 3:
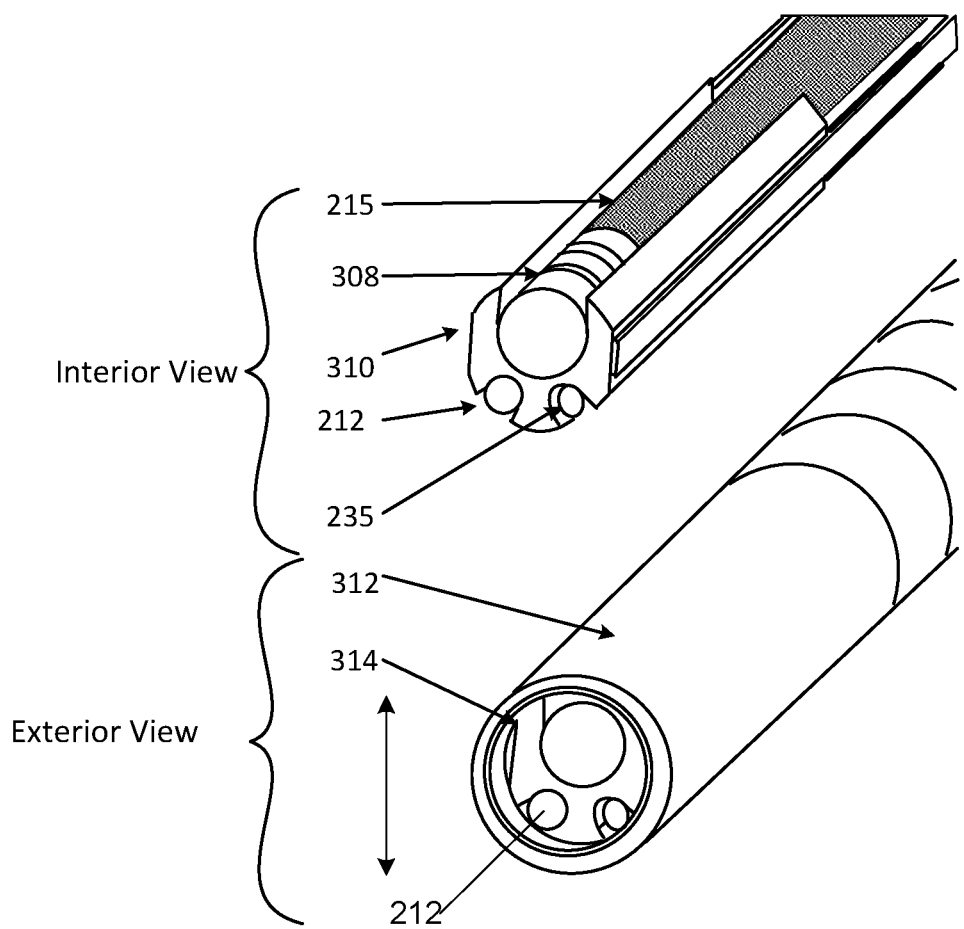
FIG. 3 is a schematic diagram of a distal end of the falloposcope.
Figure 3A:
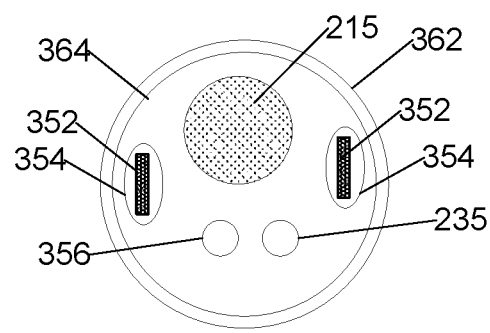
FIG. 3A is a cross sectional schematic diagram of a cross section of the falloposcope at mid-shaft.
Figure 5:
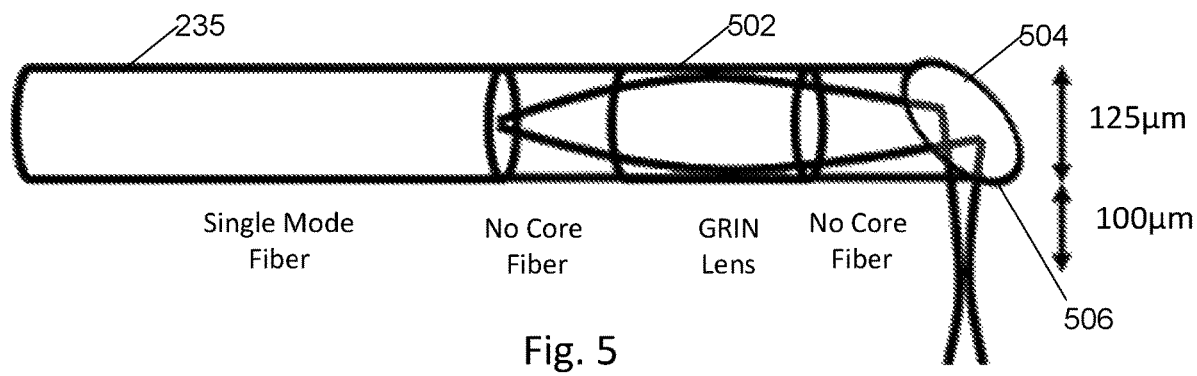
FIG. 5 is a schematic diagram of the optical coherence tomography (OCT) side-scanning optics of the distal end of an embodiment of the falloposcope.
Figure 6:
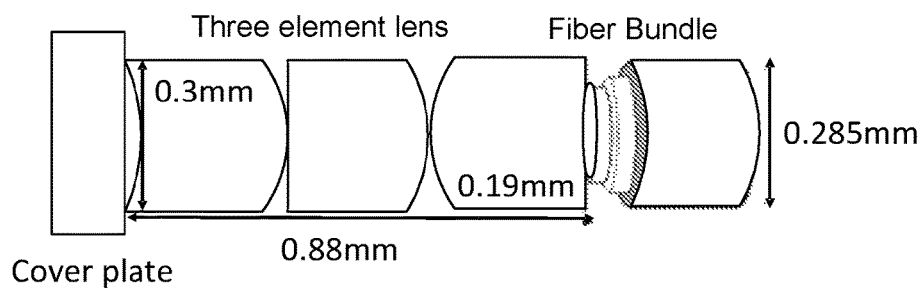
FIG. 6 is a schematic diagram of the multispectral fluorescence imaging (MFI) optics of the distal end of the falloposcope.

The distal end of a particular embodiment of the falloposcope as shown in FIG. 3 combines an imaging fiber 235 for OCT, an illumination fiber 212 for MFI, a 3,000 element 285 μm diameter coherent fiber bundle 215 for imaging and an associated micro-objective lens 308 (as shown in FIG. 6), as well as steering wires 310 for steering the tip. With custom designed optics, this achieves a full field of view of 700 at working distances of 3 to 10 mm. The distal tip of the OCT fiber 235 is lensed with GRIN lens 502 and angle polished with mirror 504 to achieve side-viewing OCT, as shown in shown in FIG. 5. A pair of steering wires 310 is provided to enable the falloposcope tip to bend approximately 60° to enable insertion through the fallopian tubes as well as to permit visualizing the fimbriae and ovary, and to permit placing the OCT channel in contact with tissue to be examined. In alternative embodiments, the OCT channel is forward viewing instead of side-viewing. In alternative embodiments, coherent fiber bundle 215 has a different, preferably greater than 3000, element count.

The falloposcope tip of FIG. 3 has a stainless steel tubular portion 312 and a transparent distal window 314 through which imaging is performed. In an alternative embodiment, stainless steel is replaced with a plastic.

OCT

The MFI ratiometric images from the MFI image processor 228 indicate regions of interest for further examination by OCT. OCT provides high resolution subsurface information of tissue microstructure permitting more precise diagnosis. The approximately 20 to 100 μm thick epithelial lining of the Fallopian tubes and ovaries should be examined for optimum cancer detection. The OCT system is designed to be side viewing and provides its highest lateral resolution at the epithelium.

The proximal OCT system is a Spectral Domain (SD-OCT) OCT system used previously with other dual modality endoscopes. The OCT has an 890 nm superluminescent diode source with full width half maximum bandwidth of 150 μm. According to the equation $\Delta z = (2 \ln 2/\pi) * (\lambda\_0^2 / \Delta \lambda)$ this corresponds to a theoretical axial resolution of 2.3 μm in air and in practice achieves sub 5 μm axial resolution in tissue. The OCT system can acquire OCT images at a rate of 4000 A-scans/s. Light from the OCT source is carried through the falloposcope by a 780HP single mode fiber 235 selected for a cut-off wavelength lower than the OCT system shortest wavelength and with a 125 μm or less cladding diameter.

The distal OCT optics as illustrated in FIG. 5 and described above are designed to achieve sub-10 μm resolution at a 100 μm depth while matching the 125 μm cladding diameter of the fiber.

Distal Electronic Camera Embodiments

Figure 6A:
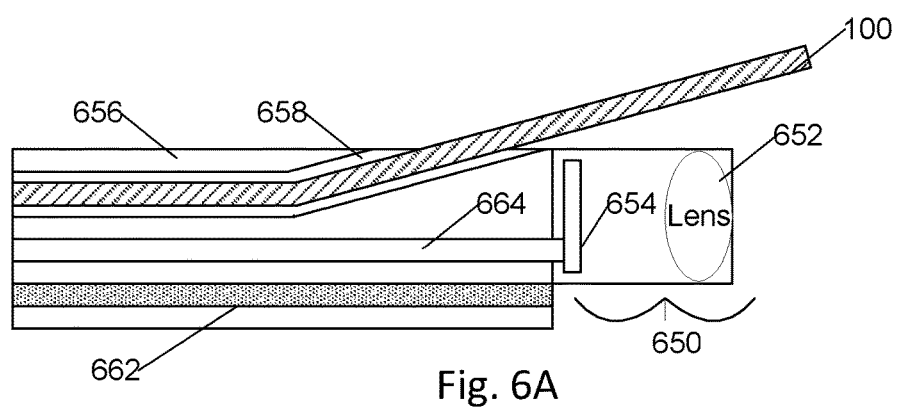
FIG. 6A is a schematic cross-sectional diagram of an embodiment having an electronic camera at the falloposcope tip.

In an alternative embodiment, instead of using an optical system having a lens located at a distal end of a coherent fiber bundle extending through the body of the falloposcope to a camera located at a proximal end of the falloposcope, an electronic camera 650 (FIG. 6A) including a lens assembly 652 and an electronic image sensor 654 is positioned at the distal end of the falloposcope body 656. In this embodiment, the camera may be a commercially available microcamera. Since available microcameras have diameters not much smaller than the diameter of the falloposcope, the OCT channel, if equipped, operates through a port on a lateral wall of the falloposcope near, but not at, the distal end of the falloposcope. Similarly, when used with a cell collection device 660, the lumen 658 within which the cell collecting device is positioned is bent at an angle, as by a wedge inserted into a slot of an extrusion used as a falloposcope body core, to exit the falloposcope through a lateral port behind the camera. In this embodiment, the cell collection device 660 may be a wire, such as a nitinol wire of 0.005-inch diameter, flexible enough to flex through the lateral port when extended by an operator to collect cells adjacent to, or ahead of the falloposcope. In these embodiments, light for the camera is provided by an efferent MFI optical fiber 662 as with the coherent-fiber-bundle embodiments, and the electronic camera is coupled through wires 664 of the falloposcope body to display and image processing equipment.

Embodiments with electronic cameras located at the distal tip of the falloposcope may perform fluorescence imaging using optical filters having a passband at the fluorescence emissions wavelength for one or more pixels in a pixel pattern and patterned onto the image sensor of the cameras, for example a 4-filter pattern of pixels may combine one fluorescence emissions filter with red, glue, and green filters for color imaging in a manner otherwise resembling Bayer-pattern filters; and patterns may have more than 4 filter colors. For example, a 9-color filter pattern is possible and could provide infrared as well as visible and fluorescence emissions filters for multiple fluorophores. Stimulus light may be provided through an efferent optical fiber in the same manner described above.

Method of Use

Figure 8:
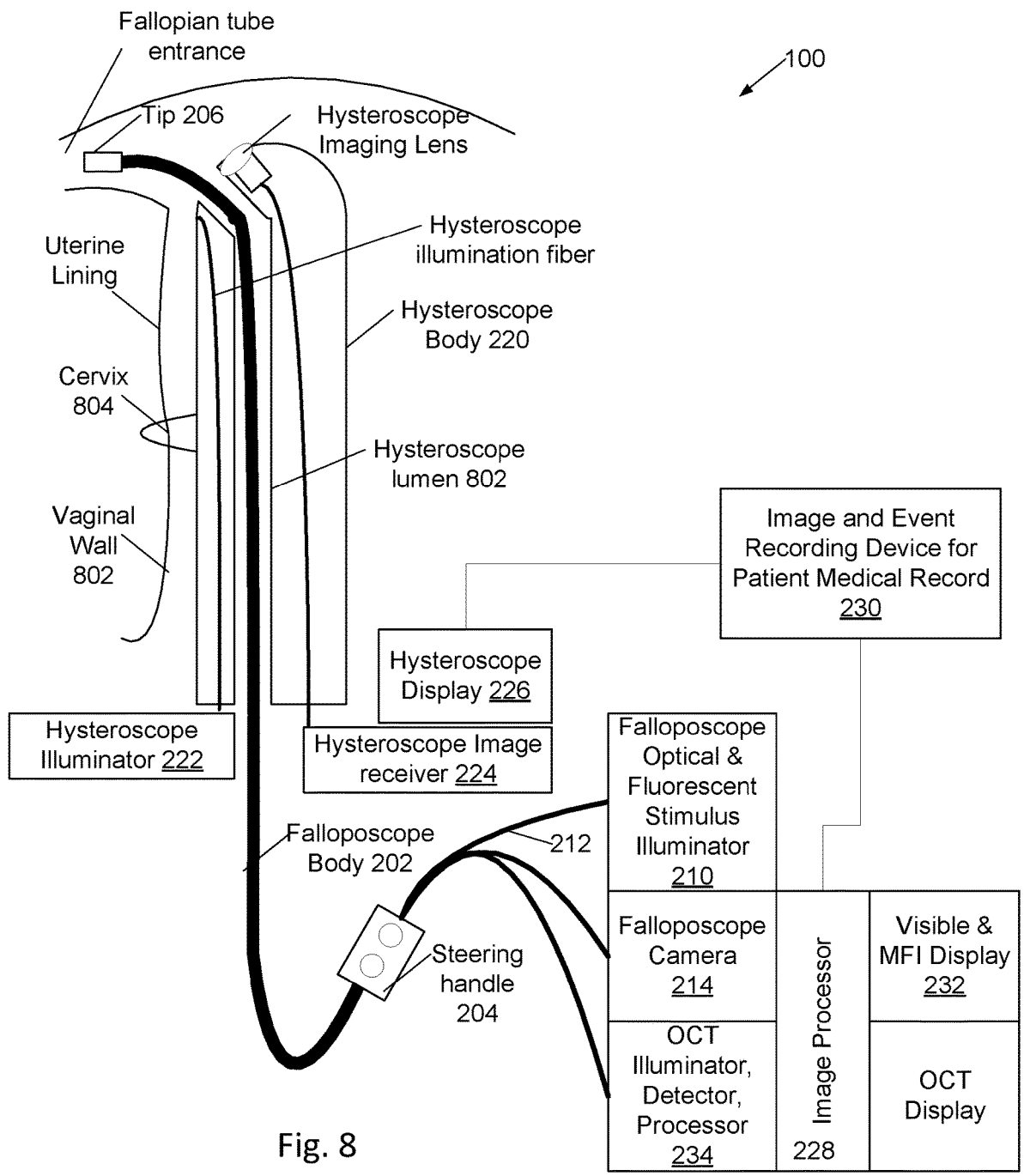
FIG. 8 is a schematic block diagram of a hysteroscope and falloposcope for use in examining a patient's ovaries and fallopian tubes, showing insertion of the falloposcope into the fallopian tube.
Figure 10:
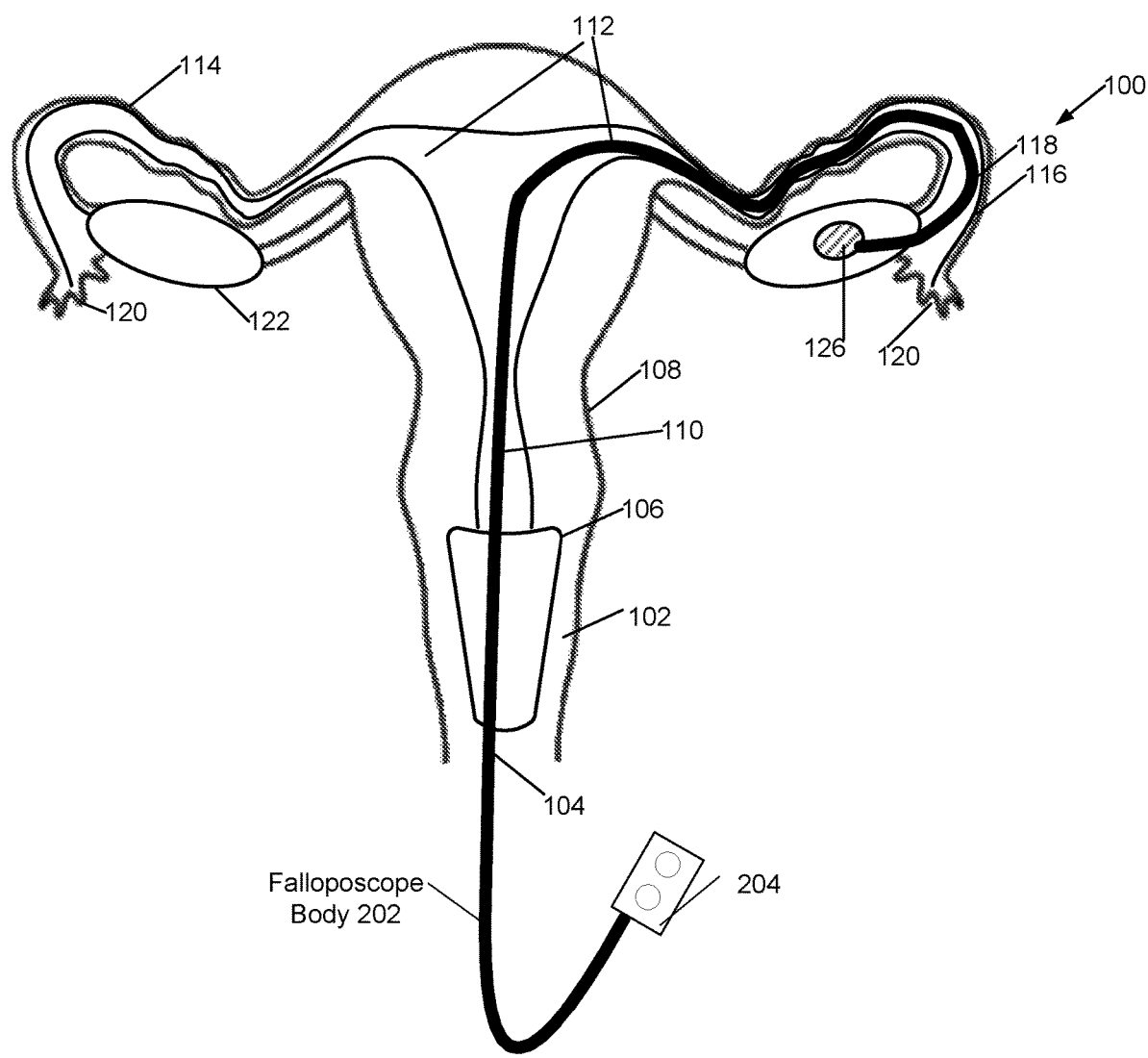
FIG. 10 illustrates a falloposcope in position for imaging abnormal tissue of an ovary.
Figure 11:
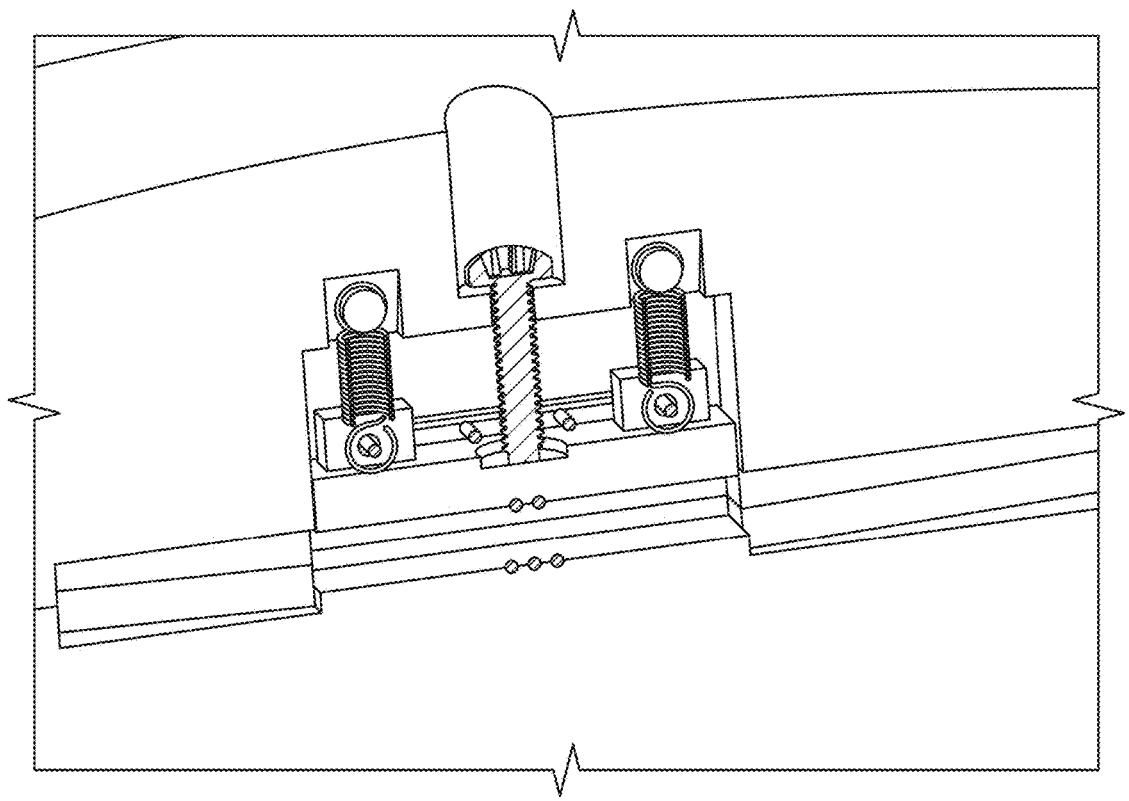
FIG. 11 illustrates a mode scrambler in the illumination fiber of the device.
Figure 12A:
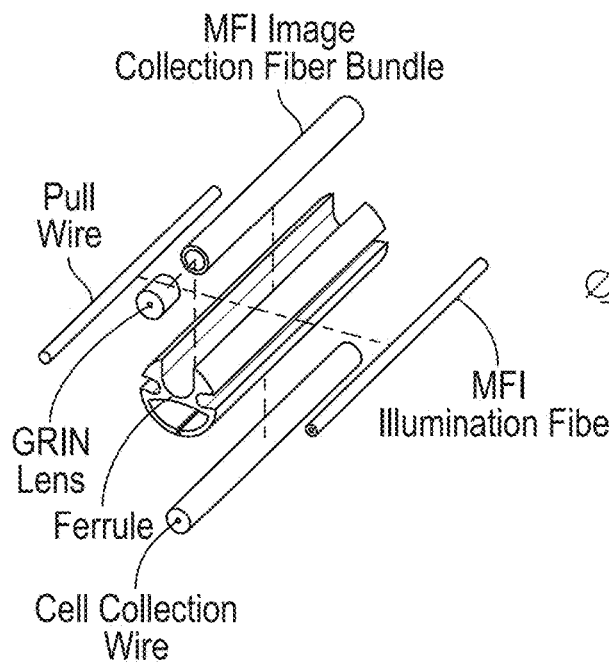
FIG. 12A and FIG. 12B represent construction of the components positioned within the falloposcope ferrule and the falloposcope ferrule.
Figure 12B:
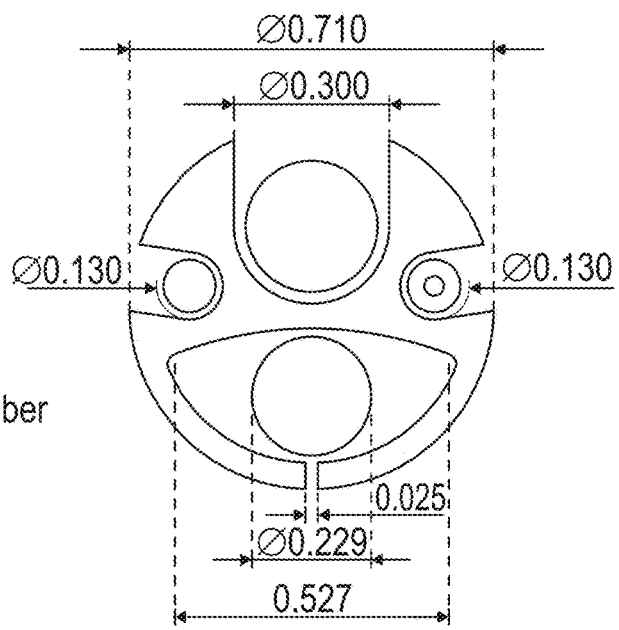
Figure 13A:
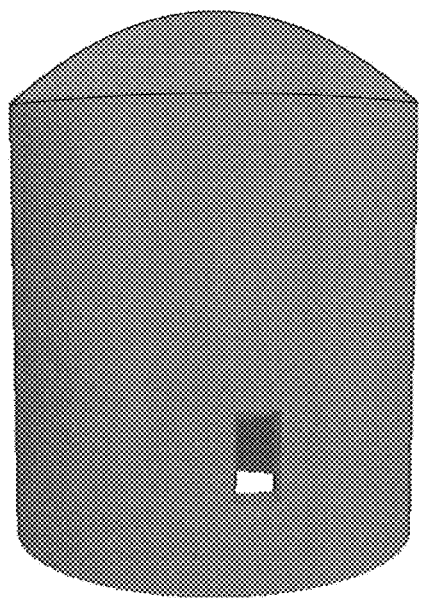
FIG. 13A is side view of the 3D printed lens.
Figure 13B:
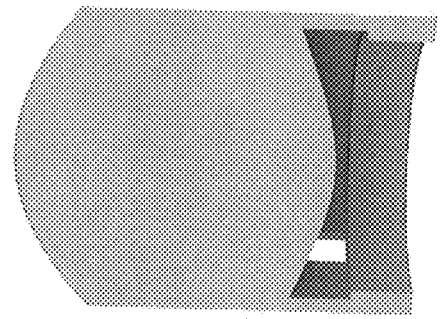
FIG. 13B is a cross sectional view of the 3-D printed lens, showing the skirt and a vent hole.
Figure 13C:
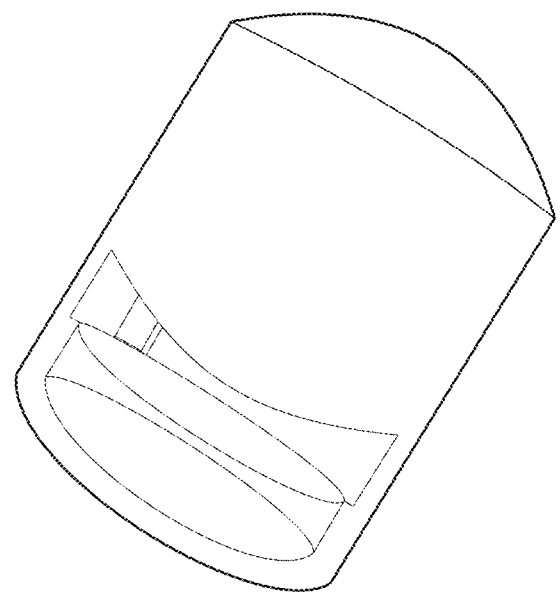
FIG. 13C is a photograph of the 3-D printed lens.

A method of using the falloposcope is outlined in FIG. 7, with reference to FIGS. 2 and 8. Falloposcope 200 is used with a hysteroscope 220 (FIG. 8), a hysteroscope illuminator 222, a hysteroscope camera 224, and a hysteroscope display 226 to assist in positioning the falloposcope into an operational position such as that illustrated in FIG. 10.

The hysteroscope 220 is inserted 704 through vagina 802 and cervix 804 into the uterus and the fallopian tube entrance is located as shown in FIG. 8.

The falloposcope is threaded into a stainless-steel insertion tube, the insertion tube is then threaded into and through the hysteroscope and its opening positioned near or within the fallopian tube entrance. The falloposcope distal tip 206 is then extended from the stainless-steel insertion tube and threaded 704 under visual guidance through the vagina, cervix, and uterus, and thence into and through the fallopian tube. Direct visual guidance is achieved through the falloposcope distal tip by providing visible-light or multiple wavelengths of stimulus light illumination through the MFI illumination fiber and performing visible-light optical imaging through the fiber bundle 215 (FIG. 2, 3). To navigate the slender and relatively flexible falloposcope through the relatively wide lumens of vagina, cervix, and uterus and thus into the fallopian tube, and since imaging through the fiber bundle is of limited resolution; additional imaging for guidance of the falloposcope through vagina, cervix, and uterus to the mouth of the fallopian tube is performed with a hysteroscope 220. The steel insertion tube also aids in positioning the very flexible falloposcope at the fallopian tube and prevents flexing of portions of the falloposcope tube body that are not in the fallopian tube. In a particular embodiment, the narrow falloposcope is threaded through the insertion tube and a lumen 802 of larger-diameter hysteroscope 220 as illustrated in FIG. 8, the hysteroscope being positioned with hysteroscope tip adjacent to the fallopian tube entrance, and the falloposcope being inserted through the hysteroscope into the fallopian tube. The distal end of the falloposcope is threaded through the fallopian tube and positioned in proximity to a first ovary of the patient. The tip of the falloposcope is manipulated, through rotation of the falloposcope, through tweaking knobs of steering handle 204 to tension the steering wires 310 to bend or straighten the tip 206, and through further insertion or partial extraction of the falloposcope body 202, to several viewing positions. The steering wires 352 are coupled to manipulation controls on a steering handle 204 similar to the manipulation controls of conventional endoscopes.

During insertion and positioning of the falloposcope, images obtained through the fiber bundle are presented on display 236 to the surgeon manipulating the falloposcope. While one purpose of these images is to allow navigation and positioning of the falloposcope head, these images also permit the surgeon to perform an optical inspection 706 of such areas as the interior of the fallopian tube and parts of the fimbriae, as well as portions of the ovary. If any suspect abnormalities, such as potentially cancerous tissues, are seen, insertion of the falloposcope is paused to permit further investigation of the suspect tissues using MFI fluorescence imaging, cell sampling, and/or optical coherence tomography; once this investigation is complete, insertion continues to the desired viewing position.

At each desired viewing position, light at a selected stimulus wavelength is emitted 708 through the MFI illumination fiber 212. While this stimulus wavelength light is being provided, fluorescence emission light is received through the fiber bundle and thence through a selected receive filter opaque to the stimulus wavelength, but transparent to at least one emission wavelength longer than the stimulus wavelength; this light is imaged to form an emission wavelength image. The received light filter is then changed to a clear or a neutral density filter and a reflected-light image is obtained. The emission wavelength image and reflected light images are processed by the image processor 228 to determine locations of any suspect tissue on the ovary, within the fimbriae, or within the fallopian tube.

In embodiments, at each viewing location, light at one or more additional stimulus wavelengths selected from the wavelengths of Table 1 and provided by the proximal optics are provided in a sequence, while the receive filter is changed so light at a second or additional emissions wavelength is imaged, to provide additional emission wavelength images. Determination of suspect tissue may be based upon one or more of the emission wavelength images obtained at each position, or on all emission wavelength images. In alternative embodiments, additional stimulus wavelength sources and paired receive filters are provided to allow additional stimulus wavelength-emissions imaging wavelength pairs.

In the event suspect abnormalities tissue is found, the tip may be further manipulated to place 710 the GRIN lens of the OCT channel in contact with the tissue to be examined, and optical coherence tomography is performed. Similarly, in embodiment having a cell sampling device, the tip may be positioned to permit the cell sampling device to scrape cells from the suspect tissue.

Once study of the first fallopian tube and ovary is completed, the method is repeated 712 for the second ovary of the patient. Throughout the procedure, images taken in both visible light and in fluorescence emissions light through the falloposcope camera 214, and images obtained through the hysteroscope 220 in embodiments using a hysteroscope, and OCT data are recorded in an image and event recording system for placement into the patient's medical record.

Figure 9:
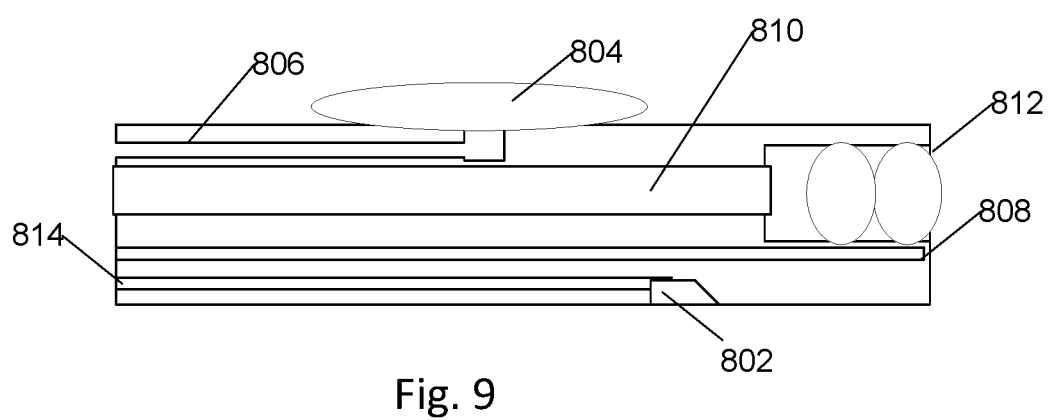
FIG. 9 is a cross sectional diagram of a falloposcope tip equipped with an everting balloon for use in positioning the falloposcope tip.

In an alternative embodiment, the falloposcope tip is fitted with an everting balloon as illustrated in FIG. 9. In use, when it is desired to ensure that the OCT port 802 is adjacent to suspect tissue, balloon 804 is inflated through a lumen 806 to press the tip against tissue. Also shown in FIG. 9 is the MFI illumination fiber 808, the coherent bundle for MFI imaging 810, an MFI lens system 812, and the OCT fiber 814.

In an alternative embodiment, instead of the external laser-based illuminator 210 shown in FIG. 4, one or more light-emitting semiconductor devices are incorporated directly into falloposcope tip and energized through a wire when light emission from the tip is desired. In embodiments, the light-emitting semiconductor devices are laser diodes, in an alternative embodiment the light-emitting semiconductor devices are light-emitting diodes.

In an alternative embodiment, instead of using a coherent fiber bundle to route images from falloposcope tip to a filter and camera located outside the patient, an electronic camera is fabricated within the falloposcope tip to capture images. In a particular embodiment, the electronic camera within the falloposcope tip has a lens adapted to focus images on a hyperspectral photosensor array, the hyperspectral photosensor array having a filter layer incorporating a tiling pattern of microfilters, with each microfilter located over a photosensor of the array, in manner similar to Bayer-pattern photosensors but with pass bands at selected fluorescence emissions wavelengths and stimulus wavelengths instead of at red, green, and blue wavelengths as with standard Bayer-pattern devices. In a particular embodiment, the hyperspectral photosensor array has a pattern of filters with passbands of 375-410 nm, 410-500 nm, 500-600 nm, 600-655 nm, and a clear filter. This embodiment is capable of performing observations at the same stimulus wavelength-emissions wavelength pairs discussed with reference to Table 1.

In another alternative embodiment, instead of a coherent fiber bundle having round or rectangular cross section with a fixed imaging lens at the falloposcope tip adapted to focus received light as images on the end of the coherent fiber bundle as previously discussed; a lens system adapted to receive light from the falloposcope tip is equipped with scanning apparatus, such as one or more mirrors deflected by piezoelectric transducers, adapted to perform a raster or line scan of an image onto a single fiber or linear coherent fiber bundle.

In yet another alternative embodiment, prior to inserting the falloposcope, a guide-wire is inserted into the uterus of the patient leading to the fallopian tube entrance. The falloposcope is fabricated with a lumen sufficiently large to fit over the guide wire, and is then inserted over the guide wire into the fallopian tube entrance.

Improvements to the Falloposcope

We have constructed embodiments of the thin flexible endoscope, between 0.25 and 1.0 mm in diameter, containing both the ability to image and collect cells from small luminal structures such as the fallopian tubes and ovaries.

The imaging channel of the falloposcope requires a lens to transmit the tissue image plane to either the distal face of the fiber bundle or to the distal image sensor array. At the size range (less than 600 μm) needed for the miniature endoscope, very limited options exist for imaging lenses. A few off-the shelf options at 500 μm or even 250 μm are limited to spherical surfaces or gradient index lenses that may introduce severe aberrations. Custom spherical lenses can be created by a few specialty shops, such as Bern Optics. Multiple-lens systems, aspherical surfaces at this diameter of optics are either are difficult or impossible to manufacture with conventional methods.

An embodiment of the falloposcope uses a 3D printed lens of less than 600 micrometers in diameter for imaging to replace the GRIN lens. The lens focuses images of the fallopian tube and ovaries from a minimum focal distance of one millimeter with a preferred focal distance ranging from 3 to 10 millimeters on a coherent fiber bundle or onto a distally located sensor array of less than 600 μm diameter. A lens was designed in OpticStudio and printed using the Photonic Professional GT1 from NanoScribe. This lens has good enough quality to replace the GRIN lens used in another embodiment of the Falloposcope. Advantages include ability to achieve same or better performance of conventional lenses with fewer elements, automatic alignment as expedited by its integral positioning skirt, rapid manufacturing, and potentially lower cost. The NanoScribe Photonic Professional GT1 printer used is a high-resolution printer using a 2-photon polymerization process printer and an optically transparent photopolymerizable material such as IP-S resin from NanoScribe) The 3D printed lens may contain aspheric surfaces, multi elements and support and alignment structures for automatic alignment with the fiber bundle or sensor array. In various embodiments, the lens diameters is in the range of 50 and 600 μm. If the lens system is not designed to be in contact with the fiber bundle or sensor array, then a mechanical alignment key, and a focal-positioning skirt, can be built in with the skirt length being the focal distance to the bundle/array.

When 3D printing the lens, a drop of the resin is put onto a glass slide and a laser is focused onto the resin by a microscope objective which polymerizes the resin to make it a solid at that point. The laser is scanned to build the structure up. Because the structure was printed onto a glass slide, a flat base of the skirt or side wall was incorporated into the design. A wall was added to extend the side of the lens facing the image plane to provide a flat surface and a stand upon which to print the lens. The length of the side wall is set so the image plane is at that flat surface making it easy to align to an imaging fiber bundle. Since the printer used a dip-in printing technique, slots were designed into the side wall to avoid trapping excess resin between the glass slide it is printed on and the lens. The lens for this falloposcope may be 250 um in diameter and about 500 um tall with an effective focal length around 400 um.

Preferred diameters are 800 μm diameter for the endoscope and 200 μm for the cell collecting device.

The lens diameter is less than 600 μm and preferred 250 μm. One could use either a fiber bundle or an image sensor. The specifications for the lens are dependent upon the exact geometry of the bundle/sensor (overall size, core/pixel size, and core-to-core/pixel spacing).

An embodiment of the falloposcope contains separate channels for imaging illumination, using a small diameter (less than 300 µm) fiber optic transmitting proximal light source(s) to the distal end of the endoscope. The fiber optic incorporates a mode scrambler in the handle of the endoscope to increase the numerical aperture of the light coming out the of fiber and used for illumination of the fallopian tube and/or ovaries. This gives a larger and more evenly illuminated area to observe. The mode scrambler is made using two 3D printed plastic plates with wires glued to them. One plate is placed flush into one half of the handle. The second plate is attached to the handle using springs and dowel pins. Once the handle is closed a screw is tightened to extend the springs and push the plates closer together until the fiber is pinched between the wires. The output light of the fiber is observed while tightening the screw to see when to stop. The net result is an increase in illumination area by up to 50 times. The mode scrambler also creates a more uniform illumination field. In a particular embodiment, the mode scrambler results in a 75-degree illumination width.

Figures 14A, 14B:
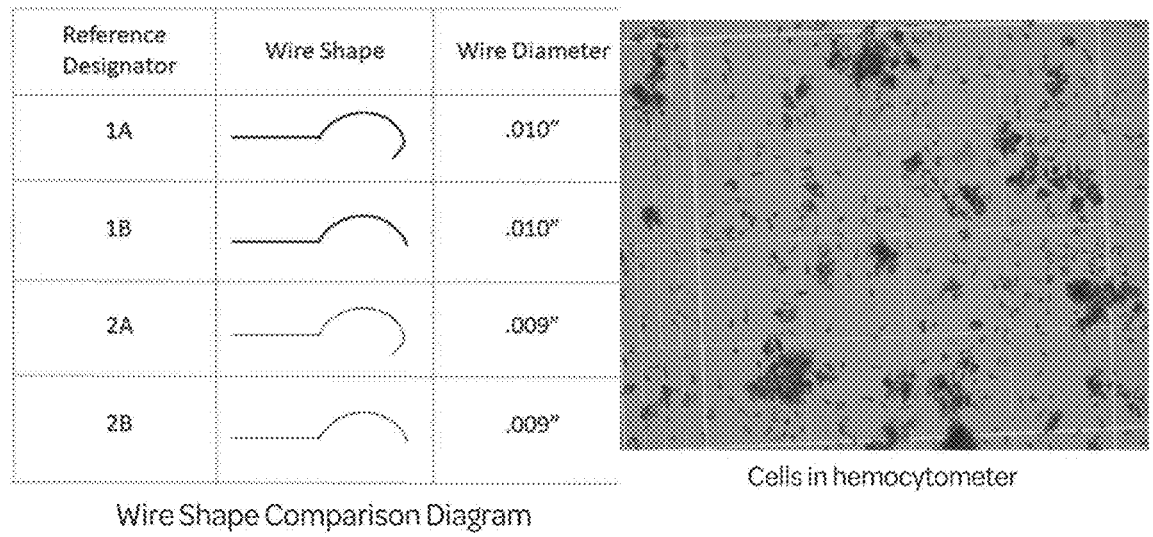
FIG. 14A is an illustration of cell sampling wires used in successful cell sampling experiments.
FIG. 14B is an illustration of stained cells sampled with the cell sampling wires.
Figure 15:
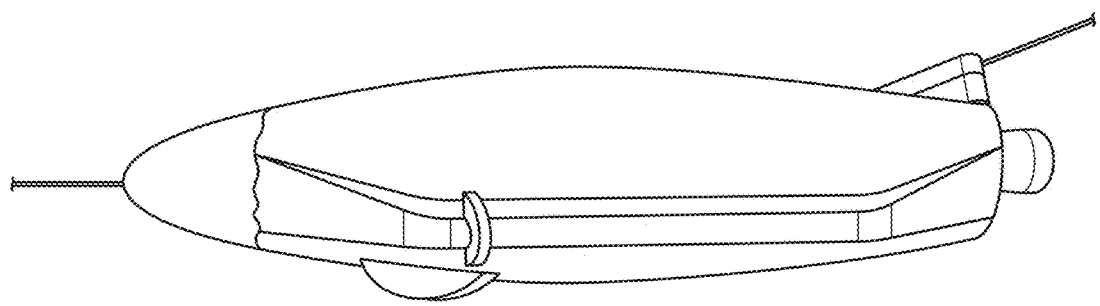
FIG. 15 is an illustration of a manipulation handle of the falloposcope.

In embodiments a cell collection device is provided using a lumen of the falloposcope that replaces one of the optical channels-typically the OCT channel—so that biological analysis can be performed instead of OCT imaging. The lumen is between 120 and 600 µm in diameter, through which a cell collecting device of between 100 and 580 µm diameter can be threaded, in particular embodiments the cell collecting device is between 178 µm (0.005 inch) diameter and 356 µm (0.010 inch) diameter. In other embodiments, the cell collecting device is a nitinol wire between 178 µm and 254 µm in diameter, the wire having an end formed into a hook as illustrated in FIG. 14A. The cell collection device is based on a thin flexible wire. In alternative embodiments, the cell collection device uses 3D printed brush bristles deposited onto to a thin flexible wire, or in another alternative embodiment the cell collection device is simply fluid introduced and aspirated back through the lumen.

In a prototype embodiment, the end of the cell collection device snipped off into an Eppendorf tube filled with phosphate-buffered saline (PBS). These tubes were centrifuged at 300 G to remove biopsy material from the wire pieces, after which the wire pieces were removed. Centrifugation was then repeated to create a cell pellet from the biopsied material. The supernatant was removed and the number of cells collected by each experimental cell collection device were counted using a hemocytometer.

In embodiments, biological analysis of cells obtained from clipping and spinning the cell collection device, washing the cell collection device, or from washing the channel into which the cell collection device may retract may include one or more of cell culture, genomics, proteomics, histology, karyometry, or other analysis techniques performed on cells and material gathered. We have prototyped cell collection devices using 0.003"-0.010" nitinol wires that can be memory formed into shepherd's hook, helical, or other shapes, extended through the distal end of the falloposcope's miniature endoscope lumen used to scrape cells, then retracted through the endoscope bearing a sampling of cells. In an alternative embodiment, the outside of the endoscope itself is textured to collect cells as it traverses the lumen of the fallopian tube.

The cell collecting device is a wire or filamentary structure which can be passed through the endoscope and extended out the distal end. Upon extension, the device effectively curves into between 0.25 and 10 mm radius as illustrated in FIG. 14A, either a single curve, compound curve, or spiral, such that the device can be forced in contact with the lumen wall or ovary on being extended from the lumen. The material of the cell collecting device may be a shape memory alloy, for instance Nitinol, or a shapeable stiff polymer such as PEEK. The may be smooth, light-oxide coated, and pickled or rough surfaced wires to provide good sample sizes of particular tissues. In use, the device is controlled (extended, retracted, and in some embodiments twisted to mechanically transfer cells from the lumen wall to the device) from the proximal end of the endoscope. A handle can conveniently contain the proximal entry for the cell collecting device and actuator for steering, if utilized. The channel for the cell collecting device may also be utilized for delivery of a substance to the luminal structure, including an imaging agent (e.g. fluorescent dye), biocompatible material for flushing the lumen and the endoscope optics, and or therapy agents. The channel may also be used for aspirating materials back from the lumen. A "Y" connector in the handle may be used for introducing the cell collecting device and introducing/aspirating substances simultaneously.

Figure 16:
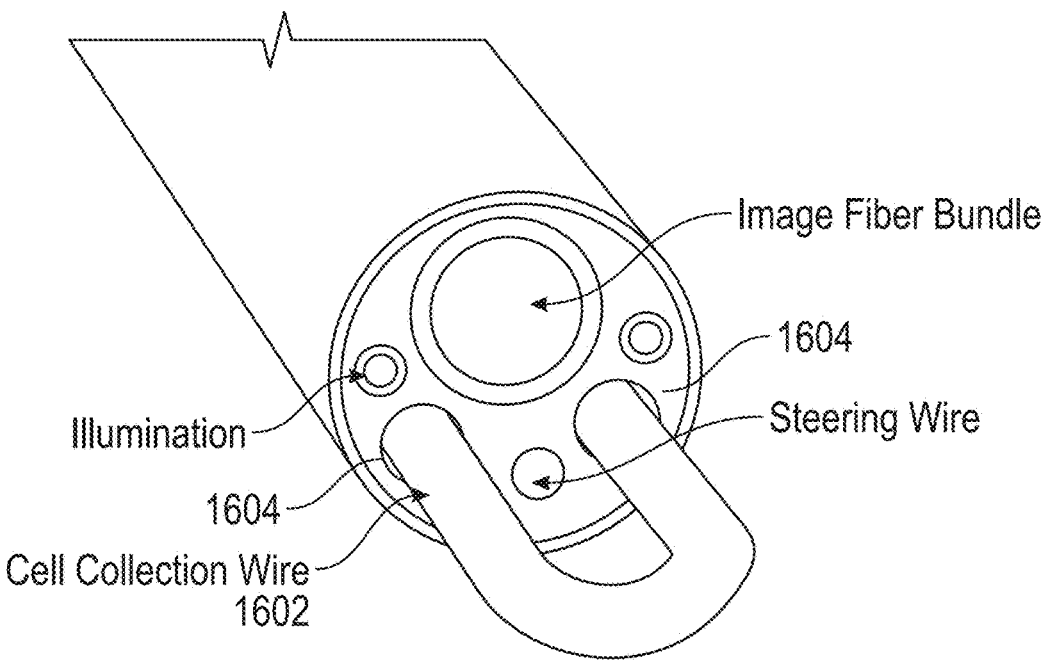
FIG. 16 is an illustration of an alternative embodiment of a cell sampling wire having a "U" shaped tip.

In an alternative embodiment, two lumens 1604 in the falloposcope body are used with a U-shaped cell collection device 1602, as illustrated in FIG. 16. In this embodiment, the U-shaped cell collection device 1602 may be a stainless steel wire.

The endoscope may optionally contain channels for a steering wire, so that the endoscope can be directed through the luminal structure or forced into contact with the lumen wall. The body of the endoscope is made from a core of flexible extruded polymer such as PEEK (polyetheretherketone), PFA, FEP, or PTFE, the extruded polymer formed as a long linear extrusion having multiple slots into which optical fibers, fiber bundles, and/or wires may be inserted. In one but not all embodiments, the extrusion is formed of multidurometer polymer to provide a stiffness graduation along the length of the falloposcope. The core is covered with thinwalled heat-shrink tubing, covering the slots forming lumens. In a particular embodiment, a thicker heat-shrink tubing is used over a proximal portion of the falloposcope to create a stiffer section, also providing a stiffness gradation along the length of the endoscope or falloposcope.

The tip of the endoscope may optionally have a stainless-steel ferrule to anchor the illumination, imaging collection, and steering wire channels, or these items may be affixed directly to the endoscope body.

Experiments

Cells were sampled using selected preformed shapes of smooth memory-alloy sampling wires in the endoscope. These cells were captured in phosphate buffered saline and centrifuged, then the pellets were resuspended in buffered saline and dyed with Trypan blue stain with little difference in cell counts captured using different sampling wire diameters. We consistently capture sufficient cells for karyotyping analysis.

Combinations

The falloposcope herein described, and its method of use, may be made using various combinations of features, some of which are detailed below.

A falloposcope designated A has an elongated body having circumferential diameter less than one millimeter, the elongated body comprising a polymer extrusion; an efferent optical fiber extending through the elongated body from a proximal end of the elongate body to a distal end of the elongate body, the efferent optical fiber having a distal end at the distal end of the elongate body; and an illuminator coupled to the efferent fiber near the proximal end of the elongate body. The falloposcope also has at least one steering wire extending through the elongate body and configured to, when pulled, bend a portion of the elongate body near the distal end of the elongate body; a lens assembly located at the distal end of the elongate body configured to focus images on a coherent fiber bundle running through the elongate body; and an electronic camera coupled to receive images from the coherent fiber bundle. The elongate body of the falloposcope has a lumen containing a cell sampling device, the cell sampling device comprising a wire, the cell sampling device extending from a sampling device handle through the elongate body from the proximal end of the elongate body to the distal end of the elongate body.

A falloposcope designated AA including the falloposcope designated A wherein the illuminator comprises a plurality of lasers coupled to provide light to the efferent fiber, the falloposcope further comprising a mode scrambler coupled to the efferent fiber between the illuminator and the elongate body, the mode scrambler configured such that an angular width of light emitted from the efferent optical fiber at the distal end of the efferent optical fiber is broader than without the mode scrambler.

A falloposcope designated AB including the falloposcope designated AA wherein the angular width of light emitted from the efferent optical fiber at the distal end of the efferent optical fiber is 75 degrees.

A falloposcope designated AC including the falloposcope designated AA or AB wherein the mode scrambler comprises multiple sharp bends of the efferent optical fiber.

A falloposcope designated AD including the falloposcope designated A, AA, AB, or AC wherein the lens assembly comprises a lens formed with an integral skirt adapted to aid centering the lens over an end of the coherent fiber bundle.

A falloposcope designated AE including the falloposcope designated AD wherein the lens with an integral skirt is formed of photopolymerized resin.

A falloposcope designated AF including the falloposcope designated A, AA, AB, AC, AD, or AE wherein the cell sampling device comprises a nitinol wire having diameter greater than or equal to 178 microns and less than or equal to 356 microns.

A falloposcope designated AG including the falloposcope designated AF wherein the cell sampling device comprises a nitinol wire having diameter greater than or equal to 178 microns and less than or equal to 254 microns.

A falloposcope designated AH including the falloposcope designated A, AA, AB, AC, AD, AE, AF, or AG wherein the cell sampling device has a roughened surface.

A falloposcope designated AJ including the falloposcope designated A, AA, AB, AC, AD, AE, AF, or AG wherein the cell sampling device has a crimped surface near a distal end of the elongated body.

A falloposcope designated AK including the falloposcope designated A, AA, AB, AC, AD, AE, AF, AG, AH, or AJ wherein the cell sampling device has a "U" shape at the distal end of the elongate body.

A falloposcope designated AL including the falloposcope designated A, AA, AB, AC, AD, AE, AF, AG, AH, AJ, AK, C, CA, or CB further including a metallic sleeve disposed about the elongated body and adapted for insertion through a hysteroscope.

A falloposcope designated AM including the falloposcope designated A, AA, AB, AC, AD, AE, AF, AG, AH, AJ, AK, AL, C, CA, or CB wherein the elongated body has a first stiffness near the distal end of the elongated body and a second stiffness greater than the first stiffness near the proximal end of the elongated body.

A method designated B of obtaining cells from a subject for examination includes inserting a falloposcope through a hysteroscope into a fallopian tube of a subject; extending the falloposcope through the fallopian tube to an ovary of the subject; extending a cell collecting device through a lumen of the falloposcope to collect the cells from the subject; withdrawing the cell collecting device into the falloposcope; and removing the cells from the falloposcope. The falloposcope includes an elongated body having circumferential diameter less than one millimeter, the elongated body having a core formed of a polymer extrusion; an efferent optical fiber extending through the elongated body from a proximal end of the elongate body to a distal end of the elongate body, the efferent optical fiber having a distal end at the distal end of the elongate body; an illuminator coupled to the efferent fiber near the proximal end of the elongate body; a lens assembly located at the distal end of the elongate body and configured to focus images on an image sensor selected from the group consisting of a camera with a coherent fiber bundle running through the elongate body, and an electronic image sensor; and the elongate body has a lumen containing the cell sampling device, the cell sampling device comprising a wire, the cell sampling device extending from a sampling device handle through the elongate body from the proximal end of the elongate body to the distal end of the elongate body.

A method designated BA including the method designated B wherein inserting the falloposcope through a hysteroscope into a fallopian tube comprises inserting the falloposcope into a metal tube, inserting the metal tube through the hysteroscope, and extending the falloposcope through the metal tube into the fallopian tube.

A falloposcope designated C includes an elongated body having circumferential diameter less than one millimeter, the elongated body comprising a polymer extrusion; a light emission port at a distal end of the elongate body, the elongate body also having a proximal end, at least one steering wire extending through the elongate body and configured to, when pulled, bend a portion of the elongate body near the distal end of the elongate body; an electronic camera located at the distal end of the elongate body; wherein the elongate body has a lumen containing a cell sampling device, the cell sampling device comprising a wire, the cell sampling device extending from a sampling device handle through the elongate body from the proximal end of the elongate body to a lateral sampling device port near the distal end of the elongate body.

A falloposcope designated CA including the falloposcope designated C wherein the light emission port comprises a distal end of an efferent optical fiber extending through the elongated body from the proximal end of the elongate body to the distal end of the elongate body; where the efferent optical fiber is coupled to an illuminator coupled to the efferent fiber near the proximal end of the elongate body.

A falloposcope designated CB including the falloposcope designated C wherein the light emission port comprises a light-emitting diode at the distal end of the elongate body.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of obtaining cells from a subject for examination comprising:
   inserting a falloposcope through a hysteroscope into a fallopian tube of a subject;
   extending the falloposcope through the fallopian tube to an ovary of the subject;
   extending a cell sampling device through a lumen of the falloposcope to collect the cells from the ovary of the subject;
   withdrawing the cell sampling device into the falloposcope; and
   removing the cells from the falloposcope;
   where the falloposcope comprises:
      an elongated body having circumferential diameter less than one millimeter, the elongated body having a core formed of a polymer extrusion;
      an efferent optical fiber extending through the elongated body from a proximal end of the elongate body to a distal end of the elongate body, the efferent optical fiber having a distal end at the distal end of the elongate body;
      an illuminator coupled to the efferent fiber near the proximal end of the elongate body;
      a lens assembly located at the distal end of the elongate body and configured to focus images on an image sensor selected from the group consisting of a camera with a coherent fiber bundle running through the elongate body, and
      an electronic image sensor; and
      the elongate body having a lumen containing the cell sampling device, the cell sampling device comprising a wire, the cell sampling device extending from a sampling device handle through the elongate body from the proximal end of the elongate body to the distal end of the elongate body;
   wherein the illuminator comprises a plurality of lasers coupled to provide light to the efferent fiber, the falloposcope comprising a mode scrambler coupled to the efferent fiber between the illuminator and the elongate body, the method further comprising:
   configuring the mode scrambler such that an angular width of light emitted from the efferent optical fiber at the distal end of the efferent optical fiber is broader than without the mode scrambler.

2. The method of claim 1 wherein inserting the falloposcope through a hysteroscope into a fallopian tube comprises inserting the falloposcope into a metal tube, inserting the metal tube through the hysteroscope, and extending the falloposcope through the metal tube into the fallopian tube.

3. The method of claim 1 wherein the angular width of light emitted from the efferent optical fiber at the distal end of the efferent optical fiber is 75 degrees.

4. The method of claim 1 wherein the mode scrambler comprises multiple sharp bends of the efferent optical fiber.

5. The method of claim 1, further comprising collecting cells with the cell sampling device comprises a nitinol wire having a diameter greater than or equal to 178 microns and less than or equal to 356 microns.

6. The method of claim 5 wherein the nitinol wire has a diameter greater than or equal to 178 microns and less than or equal to 254 microns.

7. The method of claim 6 wherein the cell sampling device has a pickled surface.

8. The method of claim 6 wherein the cell sampling device has a crimped surface near a distal end of the elongated body.

9. The method of claim 6 wherein the cell sampling device has a "U" shape at the distal end of the elongate body.

10. The method of claim 1, further comprising:
    disposing a metallic sleeve about the elongated body for insertion through a hysteroscope.

11. The method of claim 10 wherein the elongated body has a first stiffness near the distal end of the elongated body and a second stiffness greater than the first stiffness near the proximal end of the elongated body.

12. A method of obtaining cells from a subject for examination comprising:
    inserting a falloposcope through a hysteroscope into a fallopian tube of a subject;
    extending the falloposcope through the fallopian tube to an ovary of the subject;
    extending a cell sampling device through a lumen of the falloposcope to collect the cells from the ovary of the subject;
    withdrawing the cell sampling device into the falloposcope; and
    removing the cells from the falloposcope;
    where the falloposcope comprises:
       an elongated body having circumferential diameter less than one millimeter, the elongated body having a core formed of a polymer extrusion;
       an efferent optical fiber extending through the elongated body from a proximal end of the elongate body to a distal end of the elongate body, the efferent optical fiber having a distal end at the distal end of the elongate body;
       an illuminator coupled to the efferent fiber near the proximal end of the elongate body;
       a lens assembly located at the distal end of the elongate body and configured to focus images on an image sensor selected from the group consisting of a camera with a coherent fiber bundle running through the elongate body, and
       an electronic image sensor; and
       the elongate body having a lumen containing the cell sampling device, the cell sampling device comprising a wire, the cell sampling device extending from a sampling device handle through the elongate body from the proximal end of the elongate body to the distal end of the elongate body;
    wherein the lens assembly comprises a lens that is formed with an integral positioning skirt adapted to aid centering the lens over an end of the coherent fiber bundle.

13. The method of claim 12, wherein the integral skirt is formed of photopolymerized resin.

* * * * *